United States Patent [19]

Feinberg

[11] Patent Number: 4,711,855
[45] Date of Patent: Dec. 8, 1987

[54] DERIVATIVES OF 3,5,3-TRIIODOTHYRONINE

[75] Inventor: Richard R. Feinberg, Sharon, Mass.

[73] Assignee: Ciba Corning Diagnostics Corp., Medfield, Mass.

[21] Appl. No.: 698,108

[22] Filed: Feb. 5, 1985

[51] Int. Cl.[4] .................. G01N 33/534; G01N 33/543; C07D 233/00; C07D 239/00

[52] U.S. Cl. .................................. 436/500; 436/518; 436/526; 436/527; 436/804; 544/224; 544/242; 544/336; 546/329; 548/300; 548/341; 548/342; 548/356; 548/561

[58] Field of Search ............... 436/500, 518, 804; 546/329; 548/300, 341, 342, 356, 561; 544/224, 242, 336

[56] References Cited

FOREIGN PATENT DOCUMENTS 0026103 4/1981 European Pat. Off. .

Primary Examiner—Robert J. Warden
Assistant Examiner—David A. Saunders

Attorney, Agent, or Firm—D. Reitenbach

[57] ABSTRACT

A derivative of 3,5,3'-triiodothyronine having the following general formula:

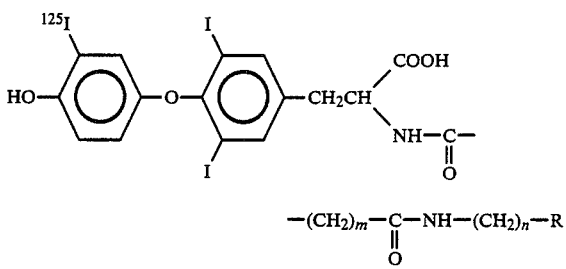

in which m is an integer from 2 to 4, n is an integer from 1 to 4, and R is a monovalent, unsubstituted, fully unsaturated five- or six-membered monocyclic heterocyclic group containing either one or two nitrogen atoms as the only hetero atoms.

12 Claims, No Drawings

DERIVATIVES OF 3,5,3-TRIIODOTHYRONINE

BACKGROUND OF THE INVENTION

The present invention relates to derivatives of 3,5,3'-triiodothyronine ($T_3$) which are useful for the measurement of free $T_3$ in a liquid sample in which the $T_3$ is present in both free and bound states.

$T_3$ is one of the two physiologically important iodinated hormones, the other one being thyroxine ($T_4$). In serum, most $T_3$ is bound to thyroxine-binding globulin (TBG), although some binding to albumin and probably thyroxine-binding prealbumin (TBPA) also occurs. Of the $T_3$ present in serum, approximately 0.2 to 0.4 percent remains free; i.e., unbound to plasma proteins. It is this free fraction that is presumably active in stimulating metabolism. Moreover, it has been estimated that 65 to 75 percent of the total metabolic effects in man is due to $T_3$. Consequently, the measurement of free $T_3$ in blood serum or plasma is of clinical interest for the prophylaxis or treatment of a variety of disorders and diseases.

SUMMARY OF THE INVENTION

In accordance with the present invention, novel derivatives of $T_3$ are provided having the following general formula:

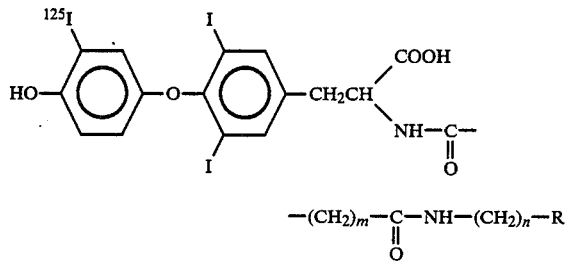

in which m is an integer from 2 to 4, n is an integer from 1 to 4, and R is a monovalent, unsubstituted fully unsaturated five- or six-membered monocyclic heterocyclic group containing either one or two nitrogen atoms as the only hetero atoms.

In a preferred embodiment, R is imidazoyl. In another preferred embodiment, m is three and n is two. In a more preferred embodiment, R is 5-imidazolyl.

The present invention also provides an immunoassay for the direct measurement of free $T_3$ in a liquid sample in which the $T_3$ is present in both free and bound states, which immunoassay comprises the steps of:

A. combining the sample with a radiolabeled derivative of $T_3$ and antibody specific for $T_3$ which is immobilized on a solid phase;

B. incubating the mixture which results from step A;

C. separating the solid phase from the liquid phase; and

D. measuring the amount of the derivative of $T_3$ present in either phase; wherein the derivative of $T_3$ has the following general formula:

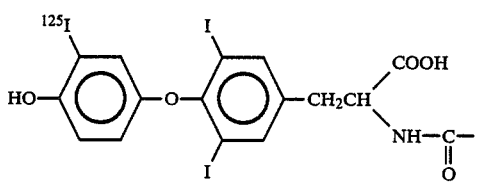

in which m is an integer from 2 to 4, n is an integer from 1 to 4, and R is a monovalent, unsubstituted, fully unsaturated five- or six-membered monocyclic heterocyclic group containing either one or two nitrogen atoms as the only hetero atoms.

DETAILED DESCRIPTION OF THE INVENTION

As already noted, m is an integer from 2 to 4 and n is an integer from 1 to 4. In preferred embodiments, m is 3 and n is 2.

R is a monovalent, unsubstituted, fully unsaturated five- or six-membered monocyclic heterocyclic group containing either one or two nitrogen atoms as the only hereto atoms. Examples of groups coming within this definition include pyrrolyl, pyrazolyl, imidazolyl, pyridyl, pyridazinyl, pyrimidinyl, and pyrazinyl. In other preferred embodiments, R is imidazolyl. In more preferred embodiments, R is 5-imidazolyl.

In the most preferred embodiment, m is 3, n is 2, and R is 5-imidazolyl.

In general, the compounds of the present invention are prepared by methods well known to those having ordinary skill in the art. In order to illustrate such preparative methods, the synthesis of the most preferred embodiment, where m is 3, n is 2, and R is 5-imidazolyl, is described in Examples 1–5, inclusive. In the Examples, all temperatures are in degrees Celsius.

EXAMPLE 1

Preparation of 3,5-Diiodothyronine Methyl Ester Hydrochloride

Five g (9.52 mmoles) of L-3,5-diiodothyronine (Sigma Chemical Company, St. Louis, Mo. 63178, Catalog No. D0629) was suspended in 50 ml of methanol (MCB, Norwood, Ohio 45212, Catalog No. MX0488-1). Dry hydrogen chloride was bubbled through the resulting suspension until the methanol was saturated with hydrogen chloride. The mixture warmed as the 3,5-diiodothyronine dissolved, resulting in a yellowish-green solution. The reaction mixture was allowed to stand for 16 hours at ambient temperature in a closed vessel. Dry hydrogen chloride was again passed through the reaction mixture. The reaction mixture was allowed to stand for an additional six hours in a closed vessel. The methanol was allowed to evaporate from the reaction mixture in a fume hood at ambient temperature, leaving 5.2 g (95% yield) of white, crystalline powder, 3,5-diiodothyronine methyl ester hydrochloride.

EXAMPLE 2

Preparation of N-Glutaryl-3,5-Diiodothyronine Methyl Ester

Four g (7.0 mmoles) of 3,5-diiodothyronine methyl ester hydrochloride was dissolved in 5.0 ml of dry N,N-dimethylformamide (VWR Scientific, Boston, Mass. 02101, Catalog No. EM-DX1726). To the resulting solution were added 3.0 ml of triethylamine (MCB, Norwood, Ohio 45212, Catalog No. TX1200-1) and 1.2 g (10.4 mmoles) of glutaric anhydride (Aldrich Chemical Company, Milwaukee, Wis. 53201, Catalog No.

6380-6). The reaction mixture then was stirred in a closed vessel for 16 hours at ambient temperature. Water was added to the reaction mixture to precipitate the product which was isolated by filtration and dried in vacuo over anhydrous calcium sulfate to give 4.2 g (92.3%) of N-glutaryl-3,5-diiodothyronine methyl ester.

EXAMPLE 3

Activation of N-Glutaryl-3,5-diiodothyronine Methyl Ester

A 10-ml amber vial containing a magnetic stirring bar was charged with 2 g (3.06 mmoles) of N-glutaryl-3,5-diiodothyronine methyl ester and 5 ml of N,N-dimethylformamide. The mixture was stirred slowly until the ester has dissolved. To the resulting solution was added 0.5 g (4.35 mmoles) of N-hydroxysuccinimide (Aldrich Chemical Company, Milwaukee, Wis. 53201, Catalog No. 13,067-2). The vial then was charged with 1.0 g (4.85 mmoles) of N,N'-dicyclohexylcarbodiimide (Pierce Chemical Company, Rockford, Ill. 61105, Catalog No. 20320) and the vial was capped and crimp sealed. The reaction mixture was stirred slowly for 16 hours at ambient temperature. The vial then was opened and charged with 400 µl of glacial acetic acid to convert excess N,N'-dicyclohexylcarbodiimide to dicyclohexylurea. The mixture was stirred for one hour at ambient temperature. The reaction mixture was filtered under suction through a scintered glass funnel to remove the dicyclohexylurea by-product. The dicyclohexylurea was washed with N,N-dimethylformamide while still on the funnel. The filtrates were combined to give a solution of activated N-glutaryl-3,5-diiodothryonine methyl ester in N,N-dimethylformamide.

EXAMPLE 4

Preparation of N-Glutarylhistamine-3,5-diiodothyronine

To a 10-ml amber vial containing a magnetic stirring bar were added 1.0 g (5.43 mmoles) of histaimine dihydrochloride (Sigma Chemical Company, St. Louis, Mo. 63178, Catalog No. H7250) and 1.60 g (15.8 mmoles) of triethylamine. The resulting mixture was stirred slowly while the activated ester solution from Example 3 was added in 1-ml portions. The vial was sealed and the reaction mixture was stirred slowly for 16 hours at ambient temperature.

The vial then was opened and the reaction mixture was added to 10 ml of 0.2N aqueous sodium hydroxide. The resulting mixture was allowed to stand for one hour, with occasional additions of small amounts of 1N aqueous sodium hydroxide solution to maintain the pH sufficiently basic. The pH was measured periodically with a wide-range (0-14) pH paper. The pH of the solution then was adjusted to between 0 and 1 with concentrated hydrochloric acid.

The acidified aqueous solution was transferred to a 250-ml separatory funnel. To the funnel were added 100 ml of water and 100 ml of ethyl acetate. The funnel was capped and shaken vigorously several times with frequent ventings. The aqueous and organic phases then were allowed to separate for one hour. The aqueous phase was drained into a 500-ml beaker. The pH was adjusted to between 6 and 7 with 1N aqueous sodium hydroxide solution. The product was isolated as a gum by precipitation with sodium chloride. The aqueous phase was decanted and the gum dissolved in minimum methanol (about 10 ml) and recrystallized by the addition of chloroform to give N-glutarylhistaimine-3,5-diiodothyronine.

EXAMPLE 5

Preparation of N-Glutarylhistaimine-3,5,$^{125}$I-3'-triiodothyronine

To a 10×75 mm glass test tube were added 100 µl of 0.10 F sodium phosphate buffer, pH 7.3, 50 µl of a solution of N-glutarylhistaimine-3,5-diiodothyronine prepared by dissolving 5.0 mg of the compound in 200 µl of N,N-dimethylformamide, and 6 mCi (about 20 µl) of an aqueous solution of sodium 125-iodide (Amersham Corporation, Chicago, Ill.). The resulting mixture was vortexed. To the test tube then was added 10 µl of a Chloramine T solution prepared by dissolving 17 mg of Chloramine T (Fisher Scientific Company, Medford, Mass. 02155, Catalog No. 0-1779) in 10 ml of dionized water. The reaction mixture was vortexed again and allowed to stand for five minutes at ambient temperature. Ten µl of a sodium metabisulfite solution prepared by dissolving 24 mg of the salt in 10 ml of deionized water was added to the tube, and the resulting mixture was vortexed. The reaction mixture was diluted with 300 µl of deionized water and vortexed.

The N-glutarylhistaimine-3,5,$^{125}$I-3'-triiodothyronine was isolated by subjecting the reaction mixture to high pressure liquid chromatography. The support was LiChrosorb RP-18 (D. Merck) in a 30-cm long column having an inner diameter of 4.6 mm. The mobile phase was 60:40 (parts by volume) methanol:0.1N acetic acid adjusted to pH 4.0 with aqueous ammonium hydroxide solution. The flow rate was 1.0 ml/min and 70-drop fractions were collected. Detection was carried out by measuring fraction absorbance at 254 nm and radioactivity. The N-glutaryl-histamine-3,5$^{125}$I-3'-triiodothyronine thus obtained was shown to be greater than 99% pure when chromatographed on an analytical column.

As already stated, the derivatives of $T_3$ described herein are useful for the measurement of free $T_3$ in a liquid sample in which the $T_3$ is present in both free and bound states. Such derivatives are especially useful in solid-phase immunoassays for free $T_3$, although the type of immunoassay, nature of the solid phase, protocols, and the like are not known to be critical. Especially suitable solid phases are finely divided particulate materials such as controlled-pore glass and magnetic particles such as those described in U.S. Pat. No. 4,554,088 incorporated herein by reference.

By way of illustration only, Example 6 describes a solid-phase immunoassay for free $T_3$ which employs finely divided controlled-pore glass as the solid phase, anti-$T_3$ antibody covalently bonded to the controlled-pore glass, and the derivative of Example 5.

EXAMPLE 6

Solid-Phase Immunoassay for Free $T_3$

The assay employed several reagents which are components of a commercially available free $T_3$ assay marketed under the IMMO PHASE ® trademark by Corning Medical and Scientific, Corning Glass Works, Medfield, Mass. 02052. These components were as follows:

Free $T_3$ standards, Catalog No. 474358, Lot No. 10313D (0.53, 1.03, 2.56, 5.56, 11.42, and 20.91 pg/ml).

Free $T_3$ controls, Catalog No. 474359, Lot No. 10313C (1.31 and 6.73 pg/ml).

IMMO PHASE® Free $T_3$ antibody, Catalog No. 474356, Lot No. 01354. This reagent consisted of anti-$T_3$ antibody covalently coupled to finely divided controlled-pore glass. Because the reagent contained merthiolate, a deblocking agent, the reagent was centrifuged and the supernatant decanted. The solid phase was washed several times with pH 7.5 0.03M phosphate buffer which contains sodium chloride at a concentration of 0.15M (PBS) and 1 mg/ml of bovine serum albumin (BSA). The solid phase then was resuspended in a volume of BSA-containing PBS equivalent to the original volume. This processed reagent will be referred to hereinafter simply as immobilized $T_3$ antibody suspension.

Tracer solution was prepared by adding an aliquot of the N-glutarylhistamine-3,5$^{125}$I-3'-triiodothyronine fraction from Example 5 to a volume of PBS containing ten percent by volume propylene glycol and 1 mg/ml of sodium salicylate to minimize nonspecific binding of the $T_3$ derivative to serum proteins, such that the resulting solution contained about 0.035 $\mu$Ci$^{125}$I.

Into duplicate 12×75 mm plastic tubes were pipetted 100 $\mu$l of standard, control, or sample, 100 $\mu$l of tracer solution, and 500 $\mu$l of immobilized $T_3$ antibody suspension. Each tube was vortexed and incubated for one hour at 37°. Each tube then was centrifuged and the supernatant decanted. The $^{125}$I activity in the solid phase then was counted.

Using the average values for each pair of duplicate standard tubes, a standard curve was generated by computer with Y: logit and x: log axes. The resulting straight line standard curve graph had a slope of $-0.80$, a Y(0) value of 0.74, and an ED50 of 8.21 pg/ml. The table below compares each actual standard concentration with the standard curve values for % B/B$_o$ and concentration.

TABLE 1

Comparison of Standard Concentrations With Calculated Values

| Standard | Calcd. % B/B$_o$ | Actual Conc.$^a$ | Calcd. Conc.$^a$ | % Diff. |
|---|---|---|---|---|
| 1 | 89.45 | 0.53 | 0.58 | 10.1 |
| 2 | 82.41 | 1.03 | 1.22 | 18.0 |
| 3 | 72.27 | 2.56 | 2.51 | −1.8 |
| 4 | 59.07 | 5.56 | 5.22 | −6.0 |
| 5 | 43.10 | 11.42 | 11.58 | 1.4 |
| 6 | 31.79 | 20.91 | 21.11 | 1.0 |

$^a$pg/ml

Tables 2 and 3 summarize the data obtained with the two free $T_3$ controls and 22 patient samples, respectively. The tables also include data obtained for the same controls and patient samples with the IMMO PHASE® two-tube free $T_3$ immunoassay kit (Corning Medical and Scientific), following the manufacturer's instructions (listed in the tables as two-tube values).

TABLE 2

Summary of Data Obtained with Free $T_3$ Controls

| Control | Actual Conc.$^a$ | Single-tube Value$^a$ | Two-tube Value$^a$ |
|---|---|---|---|
| 1 | 1.31 | 1.33 | 1.83 |
| 2 | 6.73 | 5.37 | 6.84 |

$^a$pg/ml

TABLE 3

Summary of Data Obtained with Patient Samples

| Sample I.D. | Single-tube Value$^a$ | Two-tube Value$^a$ |
|---|---|---|
| 13581 | 4.29 | 3.67 |
| 13582 | 5.28 | 4.63 |
| 13583 | 3.25 | 3.30 |
| 13584 | 4.81 | 4.06 |
| 13585 | 4.81 | 4.01 |
| 13550 | 4.61 | 3.75 |
| 13587 | 5.88 | 4.17 |
| 13588 | — | 3.06 |
| 13590 | 32.6 | 7.29 |
| 13548 | 4.80 | 4.65 |
| 13246 | 5.65 | 3.98 |
| 13245 | 5.18 | 3.88 |
| 13244 | 4.33 | 4.29 |
| 13243 | 3.93 | 3.74 |
| 13512 | 4.70 | 3.70 |
| 13511 | 5.45 | 4.35 |
| 13510 | 8.54 | 4.95 |
| 13509 | 7.22 | 4.89 |
| 13508 | 6.11 | 4.23 |
| 13507 | 4.47 | 4.30 |
| 13261 | 5.75 | 4.64 |
| 13260 | 5.03 | 4.15 |

$^a$pg/ml

The correlation coefficient for the two methods was 0.927 if the obviously aberrant data for sample 13590 were excluded.

It should be apparent to one having ordinary skill in the art that many variations are possible without departing from the spirit and scope of the invention.

What is claimed is:

1. A derivative of 3,5,3'-triiodothyronine having the following general formula:

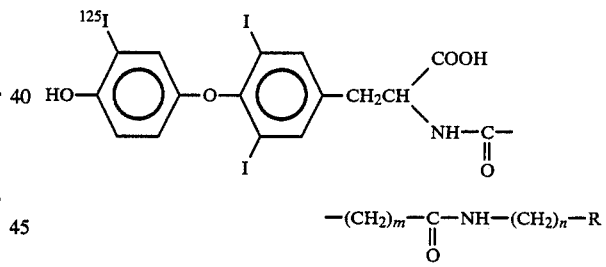

in which m is an integer from 2 to 4, n is an integer from 1 to 4, and R is a monovalent, unsubstituted, fully unsaturated five- or six-membered monocyclic heterocyclic group containing either one or two nitrogen atoms as the only hetero atoms.

2. The derivative of claim 1 in which R is imidazolyl.

3. The derivative of claim 2 in which m is 3 and n is 2.

4. The derivative of claim 1 in which m is 3, n is 2, and R is 5-imidazolyl.

5. An immunoassay for the direct measurement of free 3,5,3'-triiodothyronine in a liquid sample in which the 3,5,3'-triiodothyronine is present in both free and bound states, which immunoassay comprises the steps of:

A. combining the sample with a radiolabelled derivative of 3,5,3'-triiodothyronine and antibody specific for 3,5,3'-triiodothyronine said antibody being immobilized on a solid phase;

B. incubating the mixture which results from step A;

C. separating the solid phase from the liquid phase;

D. measuring the amount of the radiolabeled derivative of 3,5,3'-triiodothyronine present in either phase; wherein the radiolabeled derivative of 3,5,3'-triiodothyronine has the following general formula:

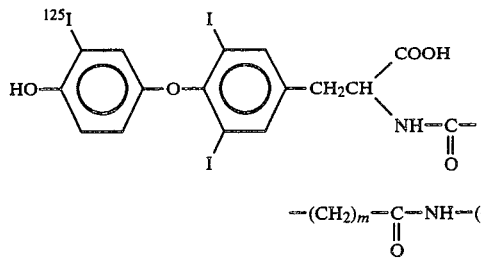

$$-(CH_2)_m-\underset{\underset{O}{\|}}{C}-NH-(CH_2)_n-R$$

in which m is an integer from 2 to 4, n is an integer from 1 to 4, and R is a monovalent, unsubstituted, fully unsaturated five- or six-membered monocyclic heterocyclic group containing either one or two nitrogen atoms as the only hetero atoms; and E. determining the free 3,5,3'-triiodothyronine from the measurement of the derivative of 3,5,3'-triiodothyronine.

6. The immunoassay of claim 5 in which m is 3, n is 2, and R is 5-imidazolyl.

7. The immunoassay of claim 6 in which the amount of the derivative of 3,5,3'-triiodothyronine in the solid phase is measured by means of the $^{125}I$ activity.

8. The immunoassay of claim 7 in which the solid phase is a finely divided particulate material.

9. The immunoassay of claim 8 in which the finely divided particulate material is controlled-pore glass.

10. The immunoassay of claim 8 in which the finely divided particulate material is magnetic.

11. The immunoassay of claim 5 wherein R is imidazolyl.

12. A derivative of 3,5-diiodothyronine having the following general formula:

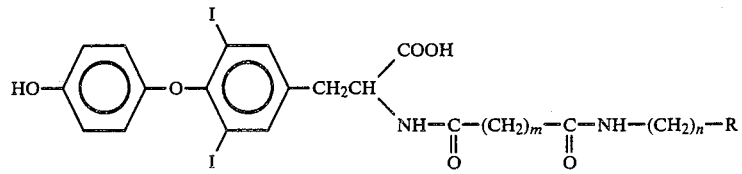

in which m is an integer from 2 to 4, n is an integer from 1 to 4, and R is a monovalent, unsubstituted, fully unsaturated five- or six-membered heterocyclic group containing either one or two nitrogen atoms as the only hetero atoms.

* * * * *